(12) United States Patent
Willis et al.

(10) Patent No.: US 10,759,776 B2
(45) Date of Patent: Sep. 1, 2020

(54) SYNTHESIS AND RESOLUTION OF NICOTINE

(71) Applicant: NJOY, LLC, Scottsdale, AZ (US)

(72) Inventors: Bert Willis, Mills River, NC (US); Mohammed Moinuddin Ahmed, Brevard, NC (US); Wesley Freund, Arden, NC (US); Douglas Sawyer, Gilbert, AZ (US)

(73) Assignee: NJOY, LLC, Scottsdale, AZ (US)

( * ) Notice: Subject to any disclaimer, the term of this patent is extended or adjusted under 35 U.S.C. 154(b) by 0 days.

(21) Appl. No.: 16/412,823

(22) Filed: May 15, 2019

(65) Prior Publication Data
US 2019/0263777 A1    Aug. 29, 2019

Related U.S. Application Data

(63) Continuation of application No. 15/727,147, filed on Oct. 6, 2017, now Pat. No. 10,329,271, which is a continuation of application No. 14/962,072, filed on Dec. 8, 2015, now Pat. No. 9,809,567.

(60) Provisional application No. 62/089,623, filed on Dec. 9, 2014.

(51) Int. Cl.
*C07D 401/04* (2006.01)
*C07D 213/80* (2006.01)
*C07D 213/803* (2006.01)

(52) U.S. Cl.
CPC ......... *C07D 401/04* (2013.01); *C07D 213/80* (2013.01); *C07D 213/803* (2013.01)

(58) Field of Classification Search
CPC .................................................. C07D 401/04
USPC ....................................................... 546/279.4
See application file for complete search history.

(56) References Cited

U.S. PATENT DOCUMENTS

| 4,386,066 | A  | 5/1983  | O'Rourke et al. |
| 5,220,068 | A  | 6/1993  | Knoll et al.    |
| 8,378,111 | B2 | 2/2013  | Divi et al.     |
| 8,884,021 | B2 | 11/2014 | Tian            |

OTHER PUBLICATIONS

Aceto et al. "Optically pure . . . " *J. Med. Chem.*, vol. 22, No. 2 pp. 174-177 (1979).
Fuhrhop et al. "Organic synthesis . . . " p. 138 (2003).
Reilly Catalog "Sodium dithionite," pp. 1-8 (2000).

*Primary Examiner* — Patricia L Morris
(74) *Attorney, Agent, or Firm* — Bookoff McAndrews, PLLC

(57) ABSTRACT

The present disclosure generally relates to methods of preparing nicotine and resolving R,S nicotine to enrich the (S)(−) enantiomer. The method may comprise combining N-methyl-2-pyrrolidone or a salt thereof with a nicotinate compound in the presence of a solvent and a strong base to form 1-methyl-3-nicotinoyl-2-pyrrolidone or a salt thereof; and reducing the 1-methyl-3-nicotinoyl-2-pyrrolidone or salt thereof in solution with $Na_2S_2O_4$ to produce racemic nicotine or salt thereof. Resolving the racemic nicotine (or other enantiomeric mixture) may comprise combining the nicotine with (−)-O,O'-di-p-toluoyl-L-tartaric acid (L-PTTA).

20 Claims, No Drawings

SYNTHESIS AND RESOLUTION OF NICOTINE

CROSS-REFERENCE TO RELATED APPLICATIONS

This application is a continuation of U.S. application Ser. No. 15/727,147 filed on Oct. 6, 2017, which is a continuation of U.S. application Ser. No. 14/962,072 filed on Dec. 8, 2015, now U.S. Pat. No. 9,809,567, which claims the benefit of priority of U.S. Provisional Application No. 62/089,623, filed on Dec. 9, 2014, each of which is incorporated by reference herein in its entirety.

TECHNICAL FIELD

The present disclosure generally relates to synthesis of nicotine and resolution of nicotine.

BACKGROUND

Nicotine (3-(1-methylpyrrolidin-2-yl)pyridine) is a compound produced naturally by plants and cultivated for a variety of medical, therapeutic, and recreational uses. As a stimulant, it is associated with various physiological effects, including increased alertness, improved mood, and enhanced movement. Nicotine occurs in nature as the (S)(−) enantiomer, which is generally understood to be more potent (e.g., more physiologically active) than the (R)(+) enantiomer. Methods of producing nicotine synthetically often result in a racemic mixture. There is a need for alternative methods of producing nicotine and obtaining individual enantiomers of nicotine.

BRIEF SUMMARY

The present disclosure includes a method of preparing racemic nicotine or a salt thereof, the method comprising: combining N-methyl-2-pyrrolidone or a salt thereof with a nicotinate compound in the presence of a solvent and a base to form 1-methyl-3-nicotinoyl-2-pyrrolidone or a salt thereof; and reducing the 1-methyl-3-nicotinoyl-2-pyrrolidone or salt thereof in solution with $Na_2S_2O_4$ to produce the racemic nicotine or salt thereof. In some embodiments, reducing the 1-methyl-3-nicotinoyl-2-pyrrolidone or salt thereof may be performed at a pH ranging from about pH 8 to about pH 11, and/or may comprise adjusting the pH while adding the $Na_2S_2O_4$ in two or more portions. In some embodiments, the nicotinate compound may comprise methyl nicotinate. The method may further comprise performing one or more processes to enrich an amount of (S)(−)-nicotine enantiomer in the racemic nicotine. In some embodiments, the racemic nicotine may comprise crude nicotine product without purification prior to enriching the (S)(−)-nicotine enantiomer. The one or more processes may comprise, for example, combining the racemic nicotine with a chiral acid, e.g., (−)-O,O'-di-p-toluoyl-L-tartaric acid (L-PTTA), and/or recrystallizing a nicotine-L-PTTA salt. In some embodiments, the L-PTTA may have a molar ratio with respect to nicotine (L-PTTA:nicotine) ranging from about 0.7 to about 0.8. The one or more processes may produce (S)(−)-nicotine with an enantiomeric excess of at least 75%, such as an enantiomeric excess of at least 90%.

The present disclosure further includes a method of preparing (S)(−)-nicotine or a salt thereof, the method comprising: reducing 1-methyl-3-nicotinoyl-2-pyrrolidone or salt thereof in solution with $Na_2S_2O_4$ to produce racemic nicotine or salt thereof; resolving the racemic nicotine by combining the racemic nicotine with (−)-O,O'-di-p-toluoyl-L-tartaric acid (L-PTTA) to produce a nicotine-L-PTTA salt; and separating (S)(−)-nicotine from the nicotine-L-PTTA salt. In some embodiments, the separated (S)(−)-nicotine may be in free base form. In some embodiments, the L-PTTA may have a molar ratio with respect to nicotine (L-PTTA:nicotine) ranging from about 0.7 to about 0.8. In some embodiments, the 1-methyl-3-nicotinoyl-2-pyrrolidone or salt thereof may be produced by combining N-methyl-2-pyrrolidone or a salt thereof with a nicotinate compound in the presence of a solvent and a base. The method may further comprise recovering unresolved nicotine, racemizing the unresolved nicotine, and/or enriching an amount of (S)(−)-nicotine enantiomer in the racemized nicotine. In some embodiments, the (S)(−)-enriched nicotine obtained from the recovered unresolved nicotine may have an enantiomeric excess of at least 90%.

DETAILED DESCRIPTION

Particular aspects of the present disclosure are described in greater detail below. The terms and definitions as used and clarified herein are intended to represent the meaning within the present disclosure. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value. As used herein, the terms "approximately" and "about" generally should be understood to encompass ±5% of a specific amount, frequency, or value.

Embodiments of the present disclosure may include producing racemic nicotine and/or resolving racemic nicotine to enrich the (S)(−) enantiomer.

Various aspects of the present disclosure may be used with and/or include one or more features disclosed in U.S. Provisional Application No. 61/826,318, filed on May 22, 2013, entitled "Compositions, Devices, and Methods for Nicotine Aerosol Delivery"; U.S. Provisional Application No. 61/856,374, filed on Jul. 19, 2013, entitled "Compositions, Devices, and Methods for Nicotine Aerosol Delivery"; U.S. Provisional Application No. 61/969,650, filed on Mar. 24, 2014, entitled "Compositions, Devices, and Methods for Nicotine Aerosol Delivery"; and/or U.S. application Ser. No. 14/284,194, filed on May 21, 2014, and published as U.S. Publication No. 2014/0345635 A1, entitled "Compositions, Devices, and Methods for Nicotine Aerosol Delivery," the disclosures of which are incorporated by reference herein in their entireties. The present disclosure may be used in accordance with aspects of U.S. Pat. No. 8,378,111 and/or U.S. Publication No. 2014/0031554.

Synthesis

Embodiments of the present disclosure include methods of producing nicotine, e.g., as a racemic mixture. For example, a pyrrolidone compound (e.g., N-methyl-2-pyrrolidone) may be combined with a suitable nicotinate compound (e.g., an ester of nicotinic acid such as methyl nicotinate, ethyl nicotinate, propyl nicotinate, isopropyl nicotinate, butyl nicotinate, or tert-butyl nicotinate) to form an intermediate, 1-methyl-3-nicotinoyl-2-pyrrolidone or a salt thereof (compound 1), which then may undergo further reaction to produce nicotine:

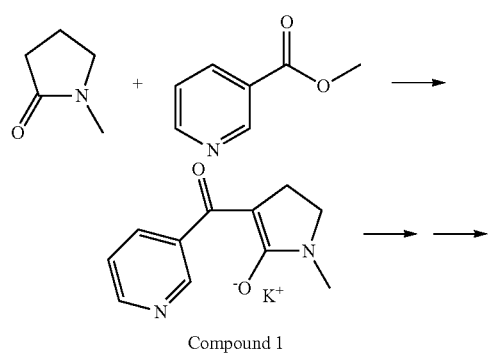

Compound 1

+/-Nicotine

The pyrrolidone compound may be reacted with methyl nicotinate in the presence of a base, e.g., a strong and/or non-nucleophilic base such as potassium tert-butoxide (KO$^t$Bu), and a suitable solvent such as toluene. Heat may be applied, e.g., under reflux, for an amount of time sufficient for the reaction to achieve a desired yield and/or purity of compound 1. In some embodiments, the reaction mixture may be heated at a temperature ranging from about 50° C. to about 150° C., such as from about 70° C. to about 130° C., about 80° C. to about 120° C., from about 90° C. to about 110° C., or from about 95° C. to about 105° C., e.g., about 100° C. The reaction mixture may be heated for a period of time ranging from about 30 minutes to about 24 hours, such as from about 1 hour to about 20 hours, from about 2 hours to about 18 hours, from about 5 hours to about 12 hours, from about 1 hour to about 5 hours, from about 1.5 hours to about 4.5 hours, from about 2 hours to about 4 hours, or from about 2.5 hours to about 3.5 hours, e.g., about 3 hours. The temperature(s) and/or reaction time(s) may be adjusted according to the specific conditions and components of the reaction mixture. Production of compound 1 may be confirmed via LCMS or other analytical identification technique.

Compound 1 may be in salt form, and may be retrieved by filtering or any other suitable separation technique, and may be washed with solvent (e.g., toluene or other suitable solvent). In some embodiments, compound 1 may be dried, e.g., under reduced pressure and/or with heat, to drive off residual solvent or other moisture prior to further reaction. The reaction may produce a yield of compound 1 greater than 75%, greater than 85%, greater than 90%, or greater than 95%, e.g., greater than 96%, greater than 97%, greater than 98%, or even greater than 99% yield. The purity of the compound 1 product may be at least 90%, e.g., about 91%, about 92%, about 93%, about 94%, about 95%, about 96%, about 97%, about 98%, or about 99% purity. In some embodiments, the purity of the compound 1 product may be greater than 99%.

Compound 1 then may undergo hydrolysis/decarboxylation. For example, compound 1 may be added to HCl (or other suitable acid) solution and heated under reflux. Drying compound 1 beforehand as mentioned above may provide for faster hydrolysis/decarboxylation. The concentration of HCl may range from about 5M to concentrated HCl (12M), such as about 6M, about 7M, about 8M, about 9M, or about 10M. The hydrolysis/decarboxylation reaction may go substantially to completion (e.g., >99% hydrolysis product) within about 24 hours, about 36 hours, about 48 hours, or about 72 hours, with more concentrated HCl solutions generally corresponding to faster reaction times.

The hydrolysis/decarboxylation reaction product may undergo reduction to yield nicotine. Exemplary reducing agents include sodium cyanoborohydride (NaBH$_3$CN) sodium triacetoxyborohydride (NaBH(OAc)$_3$), sodium borohydride (NaBH$_4$), and sodium dithionite (Na$_2$S$_2$O$_4$). The choice of reducing agent may be based on such considerations as reaction byproducts, generation of impurities, nicotine product yield, and reaction time, among other considerations. For example, NaBH$_3$CN may produce HCN, which may be unsuitable in some cases. Formation of ring-opened products and/or other impurities also may be a consideration, e.g., when selecting NaBH$_4$ as the reducing agent under certain conditions.

In some embodiments, the reducing agent may comprise Na$_2$S$_2$O$_4$. The Na$_2$S$_2$O$_4$ may be in salt form. Selecting Na$_2$S$_2$O$_4$ as a reducing agent may allow the reaction to be performed in one pot. Further, Na$_2$S$_2$O$_4$ may not cause unwanted side reactions (e.g., production of ring-opened byproducts), which could reduce the nicotine yield or lead to other undesirable results. The hydrolysis/decarboxylation reaction mixture may be basified by adding NaOH, e.g., raising the pH to a range from about 9 to about 12, e.g., a pH of about 10 or 11. The Na$_2$S$_2$O$_4$ may be added, and the pH further adjusted, e.g., to a pH of about 10 or 11, and the reaction allowed to proceed with heating from about 1 hour to about 6 hours, e.g., about 3 hours. The temperature for the reduction may range from about 40° C. to about 80° C., such as from about 50° C. to about 70° C., e.g., about 60° C. The reaction then may be quenched with water before extracting nicotine. The extraction may comprise any suitable organic solvent, including, but not limited to, dichloromethane (DCM), 2-methyltetrahydrofuran (Me-THF), ethyl acetate (EtOAc), methyl tert-butyl ether (MTBE), toluene, and cyclopentyl methyl ether (CPME). The reaction sequence according to Scheme 1 may result in a yield of racemic nicotine greater than about 30%, greater than about 35%, greater than about 40%, greater than about 45%, greater than about 50%, or greater than about 55%, having at least 90% purity, e.g., about 91%, about 92%, about 93%, about 94%, about 95%, about 96%, about 97%, about 98%, or about 99% purity. In some embodiments, the crude nicotine product may be resolved without further purification.

Resolution

Nicotine comprising a mixture of its (S)(−) and (R)(+) enantiomers (i.e., R,S nicotine) may be resolved to enrich one enantiomer with respect to the other, e.g., via an enantioselective process. The nicotine may be a racemic mixture (i.e., a 50:50 ratio of R:S) or any other mixture of enantiomers (e.g., R:S ratios of 10:90, 15:85, 20:80, 25:75, 30:70, 35:65, 40:60, 45:55, 55:45, 60:40, 65:35, 70:30, 75:25, 80:20, 85:15, 90:10, or 95:5, among other possible ratios). For example, R,S nicotine may undergo one or more processes to enrich one enantiomer with respect to the other and/or to isolate one of the enantiomers from the other. Nicotine may be resolved via a chiral compound, such as a chiral acid.

In some embodiments, the (S)(−) nicotine enantiomer may be enriched and/or isolated from the (R)(+) nicotine enantiomer, or vice versa. Compounds that may be suitable for nicotine resolution include (+)-O,O'-di-p-toluoyl-D-tartaric acid (D-PTTA) and (−)-O,O'-di-p-toluoyl-L-tartaric acid (L-PTTA), the structure of L-PTTA shown below:

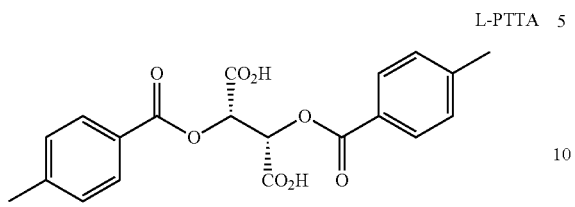

L-PTTA

In some embodiments, R,S nicotine, e.g., racemic nicotine, may be combined with L-PTTA in order to enrich the (S)(−) fraction of nicotine. In other embodiments, R,S, e.g., racemic nicotine, may be combined with D-PTTA to enrich the (R)(+) fraction of nicotine. When combined in a suitable ratio and in the presence of appropriate solvent(s), the (S)(−)-nicotine and L-PTTA may form a salt. The L-PTTA-nicotine salt may be recrystallized one or more times prior to isolation of (S)(−) nicotine in free base form:

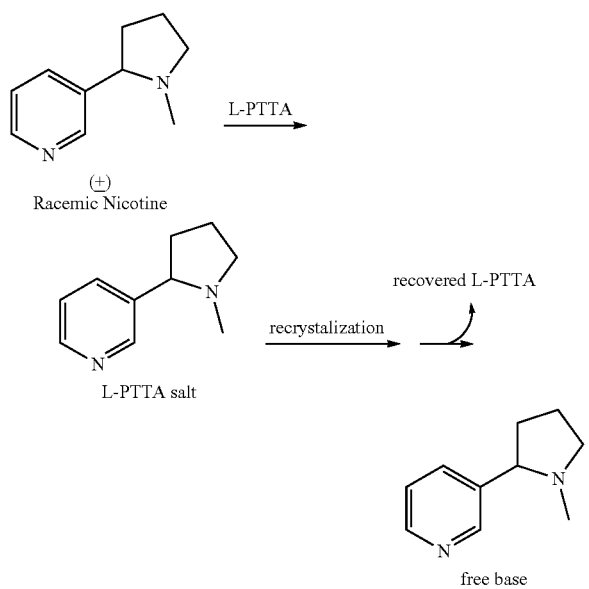

As mentioned above, the nicotine starting product may comprise crude nicotine (e.g., without purification), or may comprise nicotine product that has been subjected to one or more purification processes, such as distillation. The molar ratio of L-PTTA to nicotine may range from about 0.3 to about 1.3, such as from about 0.4 to about 1.2, from about 0.5 to about 1.1, from about 0.6 to about 1, or from about 0.7 to about 0.8. In some embodiments, for example, the molar ratio of L-PTTA to nicotine may be about 0.6, about 0.65, about 0.7, about 0.75, about 0.8, about 0.85, about 0.9, about 0.95, about 1.0, about 1.05, or about 1.1. The solvent(s) may include, but are not limited to, alcohols (e.g., isopropyl alcohol (IPA), methanol (MeOH), and ethanol (EtOH)), water, acetone, acetonitrile (MeCN), and combinations thereof. In at least one embodiment, the solvent may comprise a 3:2 ratio (v/v) of IPA:MeOH.

The solution may be heated to reflux and then cooled, e.g., to ambient or near ambient temperature. In some embodiments, seed crystals of pure (S)(−)-nicotine L-PTTA salt may be added to the solution, prior to, during, or after cooling. The L-PTTA-nicotine salt may then be filtered from solution at ambient or near-ambient temperature (e.g., a temperature ranging from about 20° C. to about 40° C., such as about 30° C.) and recrystallized one or more times. Free base nicotine ((S)(−)-nicotine-enriched product) may be isolated from the L-PTTA salt via any suitable technique. In some embodiments, for example, nicotine may be obtained from the L-PTTA salt via liquid-liquid extraction.

The structures and chirality of the nicotine L-PTTA salt and (S)(−)-nicotine-enriched product may be analyzed via any suitable technique, such as chiral HPLC. The measured optical rotation of the (S)(−)-nicotine-enriched product may range from about −140° to about −152° (EP standard). The enantiomeric excess ("ee") of the (S)(−)-nicotine-enriched product may range from about 40% to about 100%, such as from about 50% to about 99%, from about 60% to about 99%, from about 75% to about 99%, from about 85% to about 99%, from about 90% to about 99%, from about 85% to about 95%, or from about 90% to about 98%. In some embodiments, the (S)(−)-nicotine-enriched product may have an enantiomeric excess greater than about 60%, greater than about 75%, greater than about 80%, greater than about 85%, greater than about 90%, greater than about 95%, or greater than about 98%. In some embodiments, the enantiomeric excess may increase with successive recrystallizations of the L-PTTA salt prior to separation of the free base nicotine.

In some embodiments, L-PTTA may be recovered, e.g., for re-use in a subsequent enantioselective process. For example, L-PTTA may be recovered by working up (e.g., via liquid-liquid extraction) the filtrate obtained upon filtering the nicotine L-PTTA salt from solution. Additionally or alternatively, unresolved (R,S) nicotine may be recovered, e.g., to undergo a subsequent resolution process. The unresolved nicotine recovered may be a racemic mixture or any other mixture of (R) and (S) enantiomers. For example, unresolved nicotine may be recovered by working up (e.g., via liquid-liquid extraction) the filtrate obtained upon filtering the nicotine L-PTTA salt from solution. In some embodiments, the recovered nicotine may be racemized prior to undergoing subsequent resolution. For example, the recovered nicotine may be combined with KO$^t$Bu (or other suitable base or solvent) to yield a racemic mixture. The mixture of recovered nicotine and base may be heated to produce racemic nicotine. The racemic nicotine may be isolated by any suitable technique (e.g., distillation):

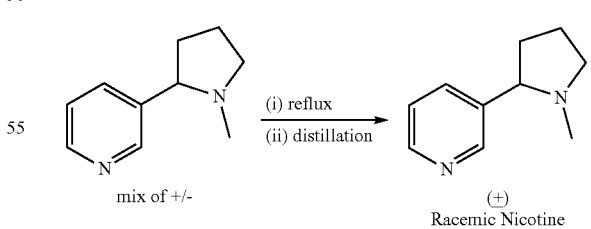

The racemic nicotine then may be combined by L-PTTA as described above to enrich the (S)(−) enantiomer.

The following examples are intended to illustrate the present disclosure without being limiting in nature. It is understood that the present disclosure encompasses additional embodiments consistent with the foregoing description and following examples.

EXAMPLES

Example 1

Nicotine Synthesis

Synthesis of Compound 1

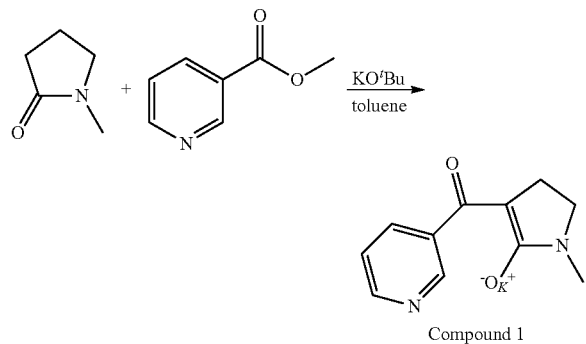

Compound 1

A 50-L, 4-neck round-bottom flask was equipped with a mechanical stirrer, a condenser with an N₂ inlet, a thermowell, and an addition funnel. The flask was charged with 1.96 kg of potassium tert-butoxide (KO$^t$Bu) (16 mol, 1 equiv.) in 24 L of toluene at room temperature (~20° C.). A white suspension was observed. N-methyl pyrrolidone (1.49 kg, 15 mol, 1.03 equiv, 1.45 L) was added and stirred for 15 minutes. A pale yellow suspension was observed. Methyl nicotinate (2 kg, 14.6 mol, 1 equiv) was added slowly as a solid over 30 minutes. A thick yellow suspension was observed. An additional 6 L of toluene was added to obtain good mixing.

The reaction mixture was heated to reflux over 1 hour at 102° C. and refluxed for 3 hours. A vigorous reaction was observed with an internal temperature of about 100° C. The heat source was removed to control the exothermic reaction and a pale yellow thick suspension was observed. After 3 hours, an aliquot of the reaction mixture was filtered and completion of the reaction was verified by LCMS (~94% product with ~6% of nicotinic acid byproduct, UV ($\lambda_{max}$) =232 nm). The reaction mixture was allowed to cool to room temperature overnight, giving a light yellow solid. The solid was filtered, washed three times with toluene (3×3 L), and dried under vacuum (25 torr) for 18 hours to give 6 kg of crude wet material appearing as a pale yellow solid cake (wet with ~40% toluene, >99% yield). Analysis by NMR and mass spectrometry (MS) was consistent with the structure of compound 1. NMR data indicated an isomeric mixture of compound 1 with residual toluene. Purity of the crude product was ~94% with about 6% nicotinic acid byproduct.

Synthesis of Nicotine

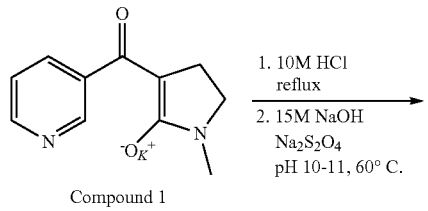

Compound 1

1. 10M HCl reflux
2. 15M NaOH
   Na₂S₂O₄
   pH 10-11, 60° C.

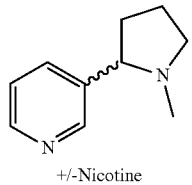

+/−Nicotine

Next, a 50-L, 4-neck round-bottom flask was equipped with a mechanical stirrer, a condenser with an N₂ inlet, a thermowell, and a stopper. The flask was charged with 7.2 L of 10M HCl, and 3.6 kg of compound 1 (crude product) was added slowly over 1 hour at room temperature to produce a dark brown solution. Vigorous gas evolved during the addition of compound 1 and a slight exotherm of 20° C. to 40° C. was observed. The solution was heated to reflux (87° C.-88° C.) over 45 minutes, and the decarboxylation reaction was monitored by aliquot LCMS using the very polar method and $\lambda_{max}$=262 nm. HCl gas evolved at the reflux temperature, and was quenched by an aqueous NaOH trap.

After 19 hours of reflux (overnight), an aliquot of the reaction mixture was quenched in water and diluted with methanol (MeOH). LCMS indicated 37% unreacted starting material, and the reflux was continued overnight a second time. After 44 hours, another aliquot was taken to determine reaction completion, with LCMS indicating ~75% product. The toluene was azeotropically removed from the reaction mixture (~2.5 kg) over 5 hours and the reflux temperature was increased to 107° C.-108° C. After 46 hours, an aliquot was again taken, with ~85% product and 15% unreacted starting material measured via LCMS. Reflux was continued overnight a third time. After 68 hours, an aliquot was taken, with about 99.4% product and 0.6% starting material measured via LCMS. The dark brown reaction mixture was allowed to cool to room temperature over the weekend (~56 hours). The brown suspension then was chilled to 5° C. using an ice/MeOH bath.

The reaction mixture was basified with the slow addition of 15M NaOH (4.5 L, adjusting the pH to ~11) over 2 hours, increasing from 5° C. to 30° C., with the exotherm controlled by the addition rate. The first of three portions of Na₂S₂O₄ was then added as a solid (1.26 kg out of 3.8 kg, 1.5 equiv.) over 5 mins at 20° C.-25° C. No significant exotherm was observed (25° C.-27° C.). The suspension was stirred for 15 mins and the pH of the reaction mixture was measured at pH~8. The pH was adjusted to pH~11 by adding 600 mL of 15M NaOH. The second portion of Na₂S₂O₄ (1.26 kg) was added over 5 mins. The suspension was stirred for another 15 mins and the pH of the reaction mixture was measured at pH~8. The pH was adjusted to pH~11 by adding 500 mL of 15M NaOH, following by addition of the third portion of Na₂S₂O₄ (1.26 kg) over 5 mins. The suspension was stirred for 15 mins and the pH adjusted to pH~11 by adding 400 mL of 15M NaOH. The reaction mixture was heated to 60° C. and stirred for 3 hours. An aliquot was taken and quenched/diluted with water, and LCMS analysis was performed using the very polar method. The LCMS analysis indicated complete consumption of the starting material, i.e., observation of only the product mass. Another aliquot was also quenched with water and extracted with MTBE and analyzed by gas chromatography (GC), which indicated 99.8% of product (e.g., complete reaction). The reaction mixture was allowed to cool to room temperature overnight.

The thick brown suspension was quenched with 15 L water and diluted with 10 L MTBE (no significant exotherm observed during quench). The organic layer was separated and the aqueous layer was extracted five times with MTBE (5×8 L). The combined organic fractions were washed twice with aqueous NaCl solution (2×4 L of brine solution), dried over $Na_2SO_4$, and filtered through a pad of $MgSO_4$. The clear filtrate was concentrated to give 780 g of crude material (33.3% yield) as a pale yellow liquid with crude purity of 99.9% as measured by GC. NMR and MS analyses were consistent with the structure of racemic nicotine. The aqueous layer was extracted twice with DCM (2×6 L). The DCM layer was separated and concentrated to give another 115 g of product with 45% purity as measured by GC. The concentrate from the DCM extraction was diluted with 1 L MTBE and washed twice with water (2×0.5 L) and twice with brine solution (2×0.5 L) to remove the high boiling impurity, dried over $Na_2SO_4$, and filtered through a pad of $MgSO_4$. The clear filtrate was concentrated to give another 44.7 g of crude material (1.9% yield) as a pale yellow liquid with crude purity of 99.8% as measured by GC. NMR and MS analyses were again consistent with the structure of racemic nicotine. The combined yield of racemic nicotine was 35.2%.

Example 2

Resolution of Racemic Nicotine

The following chiral HPLC conditions were used in all analyses: column: Chiralcel® OJ; flow rate: 1.7 mL/min; temperature: ambient; mobile phase: 95/4.98/0.02 hexanes/MeOH/trifluoroacetic acid (TFA), mixed by the HPLC pump from separate bottles of hexanes (95%) and 0.4% TFA in MeOH (5%). (Note: To ensure quality peak shape, the MeOH/TFA solution should be made fresh daily, each solvent thoroughly de-gassed, and the column given ample equilibration time (~1-2 hours).) HPLC samples were prepared as solutions of the free base in reagent alcohol (e.g., 2-5 μL injections of 5-10 mg/mL sample solutions). The free base was prepared by partitioning the salt in 1M NaOH/DCM, separating the DCM layer, drying with $MgSO_4$, filtration, DCM evaporation, and at least one co-evaporation with reagent alcohol to ensure complete DCM removal prior to subjection to the chiral HPLC column. Lastly, the sample solutions were filtered through 0.2 micron filters prior to HPLC analysis.

Enrichment of Racemic Nicotine

A 5-L, 4-neck flask equipped with a thermowell, an overhead stirrer, a condenser, and an $N_2$ inlet was charged with L-PTTA (350 g, 906 mmol, 0.73 eq). Isopropyl alcohol (IPA) (1.2 L) was added to the flask and the mixture was stirred at 20° C. To the stirring slurry was added a solution of racemic nicotine (200 g, 1233 mmol) in MeOH (800 mL). The resulting solution was stirred at 25° C. for 2 hours, and heated to reflux. After refluxing for 15 minutes, the solution was cooled to 54° C. and seed crystals of pure (−)-nicotine-L-PTTA salt (200 mg) were added. The mixture was cooled further to 25° C. (total cooling time: 3.5 hours) and stirred at 25° C. for 30 minutes.

The salt was filtered over a fritted funnel (fitted with filter paper) and rinsed with IPA (5×100 mL). The filtrate ("Filtrate 1") was set aside. The filtered solid sat covered on the filter overnight under vacuum. The solid was transferred to a 5-L flask and dried further to constant weight via rotary evaporation (T=45° C., p<30 torr), which was found to be unnecessary after 30 minutes. The yield was 303 g. Chiral HPLC of the free base of this powdery solid was 30% enantiomeric excess (ee), which was lower than a prior, pilot scale run (½₀th scale gave 50% ee).

The salt (303 g from above) was transferred to the 5-L, 4-neck flask equipped with the thermowell, the overhead stirrer, the condenser, and the $N_2$ inlet, and re-crystallized with vigorous stirring in a mixture of IPA (1.2 L) and MeOH (900 mL), which consisted of refluxing 15 mins, cooling to 58° C., seeding with pure (−)-nicotine-L-PTTA salt (200 mg), cooling further to 25° C. (3 hours total cooling time) and stirring at 25° C. for 30 minutes. The precipitated salt was filtered and rinsed with IPA (2×100 mL) and reagent alcohol (2×200 mL). The filtrate ("Filtrate 2") was set aside. The filtered solid was collected in a 5-L flask and dried to constant weight on a rotary evaporator (T=45° C., p<30 torr), yielding 205 g with 82% ee by chiral HPLC.

The salt (205 g) was transferred to the 5-L, 4-neck flask equipped with the thermowell, the overhead stirrer, the condenser, and the $N_2$ inlet, and re-crystallized with vigorous stirring in a mixture of IPA (850 mL) and MeOH (850 mL), which consisted of refluxing 15 mins, cooling to 57° C., seeding with pure (−)-nicotine-L-PTTA salt (200 mg), cooling further to 20° C. (~3.5 hours total cooling time) and stirring at 20° C. overnight (~16 hours). The precipitated solid was filtered and rinsed with IPA (5×100 mL). The filtrate ("Filtrate 3") was set aside. The filtered solid was collected in a 5-L flask and dried to constant weight on a rotary evaporator (T=45° C., p<30 torr), yielding 152 g.

Isolation of Nicotine Free Base

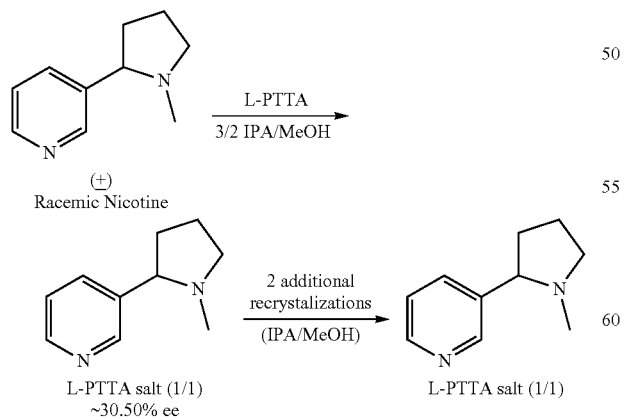

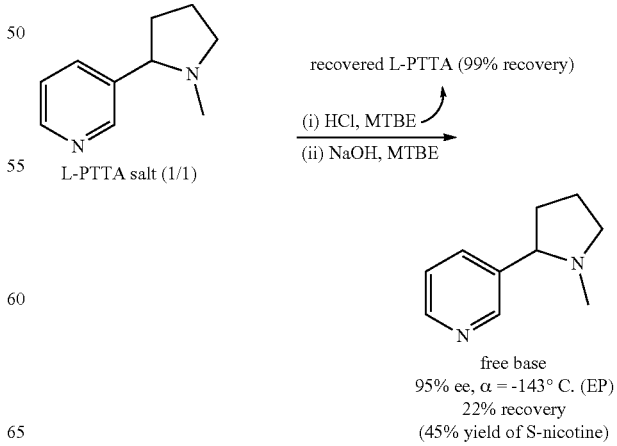

The enriched salt (152 g) was transferred to a 2-L Erlenmeyer flask, to which 1M HCl (350 mL) and MTBE (525 mL) were added. The mixture was stirred until a clear, biphasic solution was obtained (~30 mins). The mixture was transferred to a 2-L separatory funnel. The HCl layer was washed twice with MTBE (2×525 mL), and the MTBE washes ("MTBE 1") were set aside. The HCl solution was cooled in an ice bath and NaOH (10M, 45 mL) was added in several portions with stirring to adjust the solution to pH 11-12. The nicotine free base was then extracted with MTBE (2×525 mL). The MTBE extracts were dried over $MgSO_4$, filtered, and evaporated on a rotary evaporator (T=45° C., p<30 torr) for several hours, yielding 44.1 g of (S)(−)-nicotine with 1% MTBE as determined by $^1$H NMR. An additional 1 g was obtained with a third MTBE extract (525 mL) of the aqueous mixture. The yield was 44.7 g (22.3% recovery based on 200 g starting racemic nicotine). Chiral HPLC indicated 95.2% ee. A dried sample (100 mg, confirmed by $^1$H NMR) was analyzed for optical rotation (20 mg/mL solution in absolute EtOH, T=20° C.), indicating optical rotation α=−142.8° (European Pharmacopoeia standard: −140° to −152°).

Recovery of L-PTTA

Filtrates 1, 2, and 3 (see above) were combined, and the solvent was removed on a rotary evaporator (T=45° C., p<30 torr). To the residue was added 1M HCl (1.2 L) and MTBE (1.6 L), and the mixture was stirred until a clear, biphasic solution was obtained. The mixture was transferred to a 4-L separatory funnel. The HCl layer (see "Recovery of unresolved nicotine," below) was washed twice with MTBE (2×1.6 L), and the MTBE washes were combined with the "MTBE 1" extract from above. The combined MTBE solution was dried over $MgSO_4$, filtered, and evaporated, yielding a tan solid that was dried under high vacuum for several hours. The yield was 415 g of L-PTTA with 17% solvent (MTBE, IPA) as determined by $^1$H NMR; the dry yield was 345.5 g (99% recovery). The structure was confirmed by $^1$H NMR.

Recovery of Unresolved Nicotine

The HCl solution from above was cooled in an ice bath, and the pH was adjusted to pH 11-12 using a 10M NaOH solution (130 mL). The nicotine free base was extracted with MTBE (2×1.6 L), and the combined MTBE extracts were dried over $MgSO_4$, filtered, and evaporated. Drying under high vacuum at 20° C. yielded 143.3 g recovered nicotine (94% overall recovery). The structure was confirmed by $^1$H NMR with a purity of 99.9% determined via GC. Chiral HPLC indicated a 65:35 mixture of R:S (+/−) enantiomers.

Racemization of Unresolved Nicotine

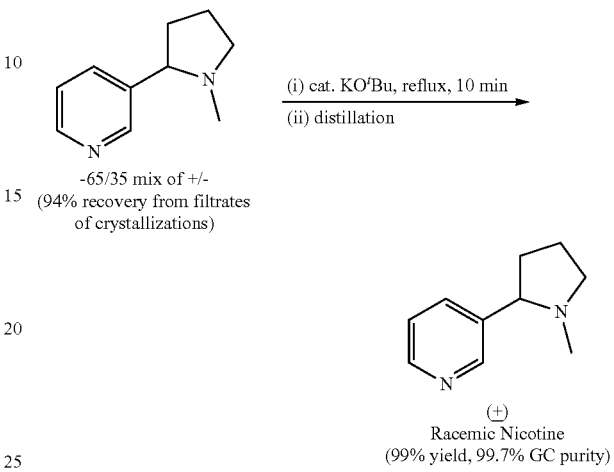

~65/35 mix of +/−
(94% recovery from filtrates
of crystallizations)

(i) cat. KO$^t$Bu, reflux, 10 min
(ii) distillation (±)
Racemic Nicotine
(99% yield, 99.7% GC purity)

A 300-mL flask was charged with KO$^t$Bu (4.4 g, 39 mmol, 4.5 mol %) and recovered nicotine (140 g of a 65:35 mixture of R:S enantiomers, 864 mmol). The mixture was heated to reflux (~240° C.) under $N_2$ for 10 minutes, whereupon chiral HPLC analysis of the mixture indicated a 1:1 mixture of R:S enantiomers. The reaction flask was cooled to <100° C. and a short-path distillation apparatus was connected to the flask. The flask was re-heated, and distillation under vacuum (boiling point 122° C. at 37 torr) afforded 138.6 g (99% yield) of a clear liquid. The purity determined via GC was 99.7%.

A series of experiments were performed to investigate the effects of different parameters on yield of (S)(−)-nicotine, ee of (S)(−)-nicotine, and optical rotation, the parameters including the type of chiral acid (i.e., L-PTTA or D-PTTA), acid equivalent to nicotine, solvent, filtration temperature, and number of salt recrystallizations. Data appear in Table 1.

TABLE 1

| Chiral Acid | Equiv. Acid | Solvent(s) | Filtration Temp. | % ee of (−)-Nicotine | # of cryst. | optical rotation | Recovery (where 50% is quantitative) | Expt. # |
|---|---|---|---|---|---|---|---|---|
| D-PTTA[1] | 1.0 | EtOH | 20° C. | 88%[3] | 2 | | 20% | 334PAL61 |
| D-PTTA | 1.0 | EtOH | 20° C. | 90%[4] | 2 | | 19% | 345PAL24 |
| D-PTTA | 1.0 | EtOH | 20° C. | 80%[4] | 1 | | — | 345PAL25 |
| D-PTTA | 1.0 | EtOH | 15° C. | 0 | 2 | | — | 345PAL14 |
| D-PTTA | 1.0 | EtOH | 20° C. | 0 | 1 | | — | 345PAL17 |
| D-PTTA | 1.0 | EtOH | 35° C. | 30% of (+) | 1 | | — | 345PAL17 |
| D-PTTA[5] | 1.0 | EtOH | 20° C. | 0 | 2 | | — | 345PAL18 |
| D-PTTA | 1.0 | MeOH | 20° C. | 30% of (+) | 1 | | — | 345PAL19 |
| D-PTTA | 1.0 | IPA/MeOH | 20° C. | 30% of (+) | 1 | | — | 345PAL20 |
| D-PTTA | 1.0 | EtOH | 20° C. | 30% of (+) | 2 | | — | 345PAL21 |
| D-PTTA | 1.0 | IPA/MeOH | 20° C. | 20% of (+) | 2 | | — | 345PAL22 |
| D-PTTA | 1.0 | EtOH:H$_2$O (95:5) | 20° C. | 8% of (+) | 2 | | — | 345PAL26 |
| D-PTTA | 1.0 | Acetone | 20° C. | 0 | 2 | | — | 345PAL27 |
| D-PTTA | 1.0 | EtOH (12.5x) | 20° C. | 0 | 1 | | — | 345PAL27 |
| L-PTTA[2] | 1.0 | EtOH | 20° C. | 40% (1$^{st}$), 73% (2$^{nd}$) | 2 | | — | 345PAL29 |
| L-PTTA | 1.0 | EtOH | 20° C. | 40%(1$^{st}$), 74% (2$^{nd}$), 88% (3$^{rd}$) | 3 | | — | 345PAL32 |
| D-PTTA | 1.1 | EtOH | 20° C. | 30% of (+) | 2 | | — | 345PAL33 |

TABLE 1-continued

| Chiral Acid | Equiv. Acid | Solvent(s) | Filtration Temp. | % ee of (−)-Nicotine | # of cryst. | optical rotation | Recovery (where 50% is quantitative) | Expt. # |
|---|---|---|---|---|---|---|---|---|
| L-PTTA | 1.0 | IPA/MeOH | 20° C. (1st), ~40° C. (2nd) | 40%(1st), 90% (2nd) | 2 | — | — | 345PAL34 |
| L-PTTA | 1.0 | IPA/MeOH | 20° C. (1st), 40° C. (2nd) | 40%(1st), 86% (2nd) | 2 | — | — | 345PAL35 |
| L-PTTA | 1.0 | IPA/MeOH | 20° C. (1st, 2nd), 40° C. (3rd) | 40%(1st), 40% (2nd), 82% (3rd) | 3 | | >50% at 20° C.; ~20% at 40° C. | 345PAL35 |
| D-PTTA | 0.6 | EtOH | 25° C. | 80% of (+) | 1 | | 18% | 345PAL36 |
| L-PTTA | 0.6 | IPA/MeOH | 25° C. | 82% | 1 | | 25% | 345PAL37 |
| L-PTTA | 0.7 | IPA/MeOH | 30° C. | 85% (1st), 95% (2nd) | 2 | | 38% (1st); 27% (2nd) | 345PAL39, 44 |
| L-PTTA | 0.7 | IPA/MeOH[8] | 30° C. | 78% | 1 | | 39% | 345PAL41 |
| L-PTTA | 0.8 | IPA/MeOH | 30° C. | 79% (1st), 95% (2nd) | 1 | −128 | 45% (1st); 30% (2nd) | 345PAL40, 46, 47 |
| L-PTTA | 0.5 | IPA/MeOH | 30° C. | 88% | 1 | | 18% | 345PAL42 |
| L-PTTA | 0.7 | IPA/MeOH | 40° C. | 86% | 1 | | 30% | 345PAL43 |
| L-PTTA | 0.7 | IPA/MeOH | 30° C. | 85% (1st), 95% (2nd), 99% (3rd) | 3 | −148 | 39% (1st); 27% (2nd); 14% (3rd, free base) | 345PAL45[9], 48 |
| — | — | — | — | 91% (Penta material spiked with racemic to 90% ee) | — | −125 | — | 345PAL47 |
| L-PTTA | 0.7 | Reagent alcohol[10] | 25° C. | 95% (2nd) | 2 | | 30% (2nd) | 345PAL49 |
| L-PTTA | 0.7 | Reagent alcohol | 25° C. | 80% (1st), 95.5% (3rd) | 3 | −142 | 35% (1st), 16% (3rd) | 345PAL50, 62 |
| L-PTTA | — | MeCN/EtOH | 25° C. | 94% | 2 | | <15% | 345PAL51 |
| L-PTTA | — | THF/MeOH | 25° C. | 93% | 2 | | <30% | 345PAL52 |
| L-PTTA | — | IPA/water | 25° C. | 94% | 2 | | 22% | 345PAL53 |
| L-PTTA | 0.7 | Reagent alcohol | 15° C. | 85% | 2 | | 22% | 345PAL54 |
| L-PTTA | 0.8 | Reagent alcohol | 25° C. | 90% | 3 | | 24% | 345PAL56 |
| L-PTTA | 0.7 | IPA/MeOH | 25° C. | 50% | 2 | | 41% | 345PAL57[11] |
| L-PTTA | 0.7 | Reagent alcohol | 25° C. | 94% | 2 | | 24% | 345PAL58[12] |
| L-PTTA | 0.7 | Reagent alcohol | 18° C. | 41% (1st), 50% (2nd), 79% (3rd) | 3 | | 54% (1st), 39% (2nd), 26% (3rd) | 345PAL60[13] |
| L-PTTA | 0.7 | Reagent alcohol | 25° C. | 71% (1st)[14] | 2 | | <15%[15] | 345PAL63 |
| L-PTTA | 0.55 | Reagent alcohol | 20° C. | 70% (1st) | 1 | | 21% | 345PAL65 |
| L-PTTA | 0.7 | 3:1 EtOH:MeOH | 25° C. | 70% (1st) | 1 | | 35% | 345PAL66 |
| L-PTTA | 0.55 | Reagent alcohol | 18° C. | 80% (1st) | 1 | | 23% | 345PAL67[16] |
| L-PTTA | 0.7 | Reagent alcohol | 25° C. | 96% (3rd) | 3 | −142 | 34% (1st), 25% (2nd), 18% (3rd) | 345PAL68[17] |
| L-PTTA | 0.7 | Mix[18] | 18° C. | 80% (1st) | 1 | | 23% | 345PAL70 |
| L-PTTA | 0.8 | Reagent alcohol | 23° C., 35° C., 25° C. | 41% (1st), 78% (2nd), 93% (3rd) | 3 | −138 | >50% (1st), 32% (2nd), 24% (3rd) | 345PAL71 |
| L-PTTA | 0.8 | Reagent alcohol + MeOH | 40° C., 35° C., 30° C. | 45% (1st), 72% (2nd), 89% (3rd) | 3 | | 50% (1st), 31% (2nd), 20% (3rd) | 345PAL72 |
| L-PTTA | 0.73 | IPA/MeOH | 25° C. (1st, 2nd), 15° C. (3rd) | 51% (1st), 84% (2nd), 96% (3rd) | 3 | | 43% (1st), 30% (2nd), 22% (3rd; free base) | 345PAL76 |
| L-PTTA (200 g nicotine) | 0.73 | IPA/MeOH | 25° C. (1st, 2nd), 20° C. (3rd) | 31% (1st), 82% (2nd), 95% (3rd) | 3 | −143 | 45% (1st), 30% (2nd), 22% (3rd; free base) | 345PAL78[19] |

[1]D-PTTA = di-p-toluoyl-D-tartaric acid.
[2]L-PTTA = di-p-toluoyl-L-tartaric acid.
[3]Purity of racemic nicotine was 90-95% (NMR).
[4]Purity of racemic nicotine was 83% (GC).
[5]Used D-PTTA from Aldrich (same material used in original 334PAL61 experiments), whereas all other 345PAL experiments used D-PTTA from Chem-Impex.
[8]Used less MeOH in this experiment to investigate the effect MeOH content has on yield and chiral purity.
[9]Crude (99% pure, non-distilled) racemic nicotine was used and in all subsequent experiments.
[10]Reagent alcohol (EtOH denatured with 5% MeOH and 5% IPA) used hereafter as solvent volumes are decreased by 65% compared with IPA/MeOH.
[11]Cooled more slowly and used less solvent (~½ the volume used in previous experiments with IPA/MeOH).
[12]Used 20% less alcohol (saturating).
[13]10 g scale, slow-cooled to ambient (18° C.) in water bath overnight, except for 3rd crystallization, which was stirred at 25° C. overnight.
[14]At this stage, % ee by HPLC was determined by integration of a ~16 minute region rather than the major peaks only. This resulted in a lower value of % ee. This approach was taken after HPLC analysis of a standard sample (900 mg of pure (−)-nicotine mixed with 100 mg racemic nicotine) showed ~95% ee by integration of the major peaks, when the actual % ee was 90%. A value of 91% ee (HPLC) for this standard was achievable if the entire ~16 minute region was integrated. As a consequence, % ee values in the earlier experiments (345PAL14 through 345PAL62) appeared to be higher (larger difference in the lower % ee values) than they actually were.
[15]Used 2x the volume of ROH to see if % ee could be increased.
[16]10 g scale, slow-cooled to ambient (18° C.) in water bath overnight.
[17]Heated at 60° C. overnight to ensure salt formation, and recrystallized with lower ROH volumes (~4 mL/g salt). Also, filtered the 3rd crystallization at 20° C. to improve recovery.
[18]Used 100% IPA for 1st crystallization, 1:1 IPA:ROH for 2nd, and ROH only for 3rd.
[19]200 g scale reaction; recovered 143.3 g unresolved free nicotine (94% recovery) and 345.5 g L-PTTA (99% recovery).

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

What is claimed is:

1. A method of preparing a nicotine composition, the method comprising:
   combining nicotine with (−)-O,O'-di-p-toluoyl-L-tartaric acid (L-PTTA) in a molar ratio of L-PTTA to nicotine ranging from about 0.3 to about 1.3, wherein the nicotine comprises a mixture of (S)-(−)-nicotine and (R)-(−)-nicotine, and wherein the (S)-(−)-nicotine and the L-PTTA form a salt; and
   separating at least a portion of the (S)-(−)-nicotine from the salt.

2. The method of claim 1, wherein the nicotine composition has an enantiomeric excess of (S)-(−)-nicotine greater than 60%.

3. The method of claim 1, wherein the nicotine composition has an enantiomeric excess of (S)-(−)-nicotine greater than 95%.

4. The method of claim 1, wherein the molar ratio of L-PTTA to nicotine ranges from about 0.5 to about 1.1.

5. The method of claim 1, wherein the molar ratio of L-PTTA to nicotine ranges from about 0.7 to about 0.8.

6. The method of claim 1, further comprising recrystallizing the salt before separating the (S)-(−)-nicotine from the salt.

7. The method of claim 1, wherein the nicotine and the L-PTTA are combined in a solution comprising an alcohol, water, acetone, acetonitrile, or a combination thereof.

8. The method of claim 7, further comprising separating the salt from the solution before separating the (S)-(−)-nicotine from the salt.

9. The method of claim 8, further comprising recovering unresolved nicotine from the solution after separating the salt from the solution.

10. The method of claim 9, further comprising enriching an amount of (S)-(−)-nicotine in the unresolved nicotine.

11. The method of claim 8, further comprising recovering L-PTTA from the solution after separating the salt from the solution.

12. The method of claim 8, further comprising adding a pure (S)-(−)-nicotine L-PTTA salt to the solution before separating the (S)-(−)-nicotine from the solution.

13. A method of preparing a nicotine composition, the method comprising:
   combining nicotine with (−)-O,O'-di-p-toluoyl-L-tartaric acid (L-PTTA) in a molar ratio of L-PTTA to nicotine ranging from about 0.6 to about 1 in solution, wherein the nicotine comprises a mixture of (S)-(−)-nicotine and (R)-(−)-nicotine, and wherein the (S)-(−)-nicotine and the L-PTTA form a salt; and
   separating at least a portion of the (S)-(−)-nicotine from the salt.

14. The method of claim 13, further comprising recovering unresolved nicotine from the solution after separating the (S)-(−)-nicotine from the salt.

15. The method of claim 14, wherein the nicotine composition has an enantiomeric excess of (S)-(−)-nicotine greater than 60%.

16. The method of claim 13, wherein the mixture of (S)-(−)-nicotine and (R)-(−)-nicotine is a racemic mixture.

17. The method of claim 13, further comprising recrystallizing the salt before separating the (S)-(−)-nicotine from the salt.

18. A method of preparing a nicotine composition, the method comprising:
   combining nicotine with (−)-O,O'-di-p-toluoyl-L-tartaric acid (L-PTTA) in a molar ratio of L-PTTA to nicotine ranging from about 0.6 to about 1, wherein the nicotine comprises a mixture of (S)-(−)-nicotine and (R)-(−)-nicotine, and wherein the (S)-(−)-nicotine and the L-PTTA form a salt; and
   separating at least a portion of the (S)-(−)-nicotine from the salt;
   wherein the nicotine composition has an enantiomeric excess of (S)-(−)-nicotine greater than 90%.

19. The method of claim 18, wherein the nicotine and the L-PTTA are combined in solution, the method further comprising adding a pure (S)-(−)-nicotine L-PTTA salt to the solution.

20. The method of claim 18, further comprising recrystallizing the salt before separating the (S)-(−)-nicotine from the salt.

* * * * *